(12) United States Patent
Meshchaninov et al.

(10) Patent No.: US 11,890,398 B2
(45) Date of Patent: Feb. 6, 2024

(54) AIR CLEANING DEVICE

(71) Applicants: Mikhail Aleksandrovich Meshchaninov, Zhukovskiy (RU); Dmitrii Yanovich Agasarov, Krasnodar (RU); Anton Viktorovich Sergeev, Krasnodar (RU)

(72) Inventors: Mikhail Aleksandrovich Meshchaninov, Zhukovskiy (RU); Dmitrii Yanovich Agasarov, Krasnodar (RU)

(73) Assignees: Mikhail Aleksandrovich Meshchaninov, Zhukovskiy (RU); Dmitrii Yanovich Agasarov, Krasnodar (RU); Anton Viktorovich Sergeev, Krasnodar (RU)

( * ) Notice: Subject to any disclaimer, the term of this patent is extended or adjusted under 35 U.S.C. 154(b) by 0 days.

(21) Appl. No.: 18/220,899

(22) Filed: Jul. 12, 2023

(65) Prior Publication Data

US 2023/0347008 A1   Nov. 2, 2023

Related U.S. Application Data

(63) Continuation of application No. PCT/IB2022/058937, filed on Sep. 21, 2022.

(30) Foreign Application Priority Data

Feb. 17, 2022 (RU) .................................. 2021140157

(51) Int. Cl.
*A61L 9/22* (2006.01)
*H05H 1/24* (2006.01)

(52) U.S. Cl.
CPC ............... *A61L 9/22* (2013.01); *H05H 1/473* (2021.05); *H05H 2245/15* (2021.05)

(58) Field of Classification Search
None
See application file for complete search history.

(56) References Cited

U.S. PATENT DOCUMENTS 4,541,848 A * 9/1985 Masuda .................. H03K 3/55
96/54
5,695,619 A * 12/1997 Williamson ........... B01D 53/32
204/170

(Continued)

FOREIGN PATENT DOCUMENTS

CN       1316615 A        10/2001
CN       2681825 Y   *    4/2004

(Continued)

OTHER PUBLICATIONS

Civitano, 'Industrial Application of Pulsed Corona Processing to Flue Gas', 1993, NATO ASI Series, vol. G 34, Part B Non-Thermal Plasma Techniques for Pollution Control (Year: 1993).*

(Continued)

*Primary Examiner* — Eliza W Osenbaugh-Stewart
(74) *Attorney, Agent, or Firm* — Bardmesser Law Group

(57) ABSTRACT

Invention relates to air cleaning systems, particularly to electric air cleaners, and may be used for decontamination of air in different industries. Invention is directed to attaining a technical effect of providing an air cleaning device, where air is cleaned owing to action of corona discharge streamers on air molecules and contamination particles. Technical effect is attained by air cleaning device that contains a high-voltage pulse generator, an outer electrode provided as a grounded metal tube, and an inner electrode rigidly secured along the tube axis by a fastening member and provided in form of a metal rod and configured so as pulsed corona discharge streamers are formed in between the inner and outer electrodes, wherein the inner electrode is spaced by a gap from an output electrode of high-voltage pulse (Continued)

generator and size of the gap assures breakdown of the gap with pulses formed by high-voltage pulse generator.

9 Claims, 1 Drawing Sheet

(56) References Cited

U.S. PATENT DOCUMENTS

| | | | |
|---|---|---|---|
| 2005/0021102 A1 | 1/2005 | Ignagni et al. | |
| 2006/0071608 A1* | 4/2006 | Malik | H05H 1/24 315/111.01 |
| 2008/0208280 A1 | 8/2008 | Lindenthaler et al. | |
| 2013/0318947 A1 | 12/2013 | Malik et al. | |
| 2014/0142652 A1 | 5/2014 | Francois et al. | |
| 2016/0067485 A1 | 3/2016 | Lindenthaler et al. | |
| 2019/0210038 A1* | 7/2019 | Kuroi | B03C 3/368 |
| 2020/0164207 A1 | 5/2020 | Meyyappan et al. | |
| 2020/0282086 A1* | 9/2020 | Silverman | A61L 9/015 |
| 2021/0104906 A1 | 4/2021 | Wang et al. | |

FOREIGN PATENT DOCUMENTS

| | | |
|---|---|---|
| CN | 103204467 A | 7/2013 |
| CN | 103368447 A | 10/2013 |
| CN | 205288095 U | 6/2016 |
| CN | 110995050 A | 4/2020 |
| EA | 012275 B1 | 8/2009 |
| ES | 2909949 A1 | 5/2022 |
| FR | 1237539 A | 7/1960 |
| GB | 516158 A | 12/1939 |
| JP | H08299747 A | 11/1996 |
| KR | 20080050318 A | 6/2022 |
| KZ | 24850 A4 | 11/2011 |
| RU | 2116244 C1 | 7/1998 |
| RU | 2122519 C1 | 11/1998 |
| RU | 12220 U1 | 12/1999 |
| RU | 61705 U1 | 3/2007 |
| RU | 2326487 C2 | 6/2008 |
| RU | 2410835 C1 | 1/2011 |
| RU | 122466 U1 | 11/2012 |
| RU | 2592085 C1 | 7/2016 |
| RU | 2741004 C1 | 1/2021 |
| RU | 2753275 C1 | 8/2021 |
| UZ | 5108 B | 4/2002 |
| UZ | 4426 C | 10/2011 |
| WO | 2012/044875 A1 | 5/2012 |

OTHER PUBLICATIONS

Search report in PCT/IB2022/060911, dated Feb. 28, 2023.
Search report in PCT/IB2022/058934, dated Dec. 15, 2022.
Search report in PCT/IB2022/058935, dated Dec. 22, 2022.
Search report in PCT/IB2022/058937, dated Dec. 15, 2022.
Search report in PCT/IB2022/060872, dated Mar. 2, 2023.
Search report in PCT/IB2022/060909, dated Mar. 2, 2023.

* cited by examiner

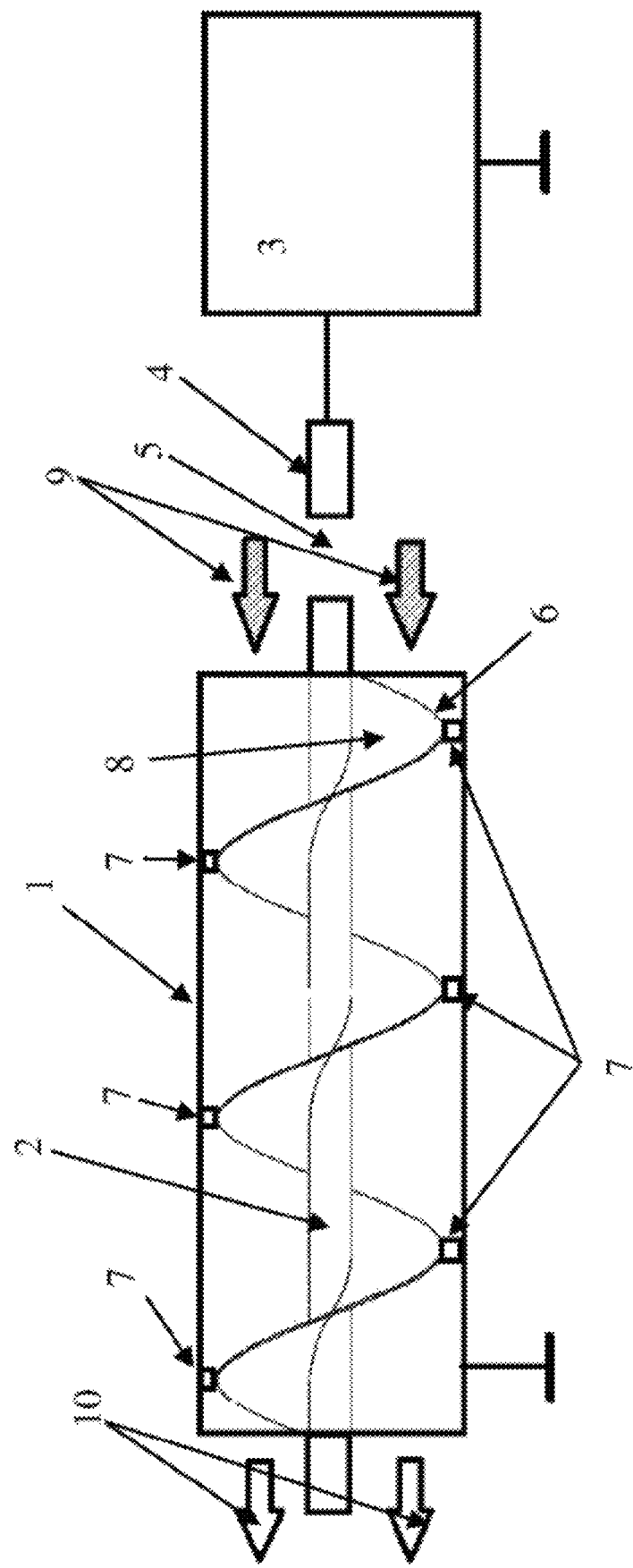

AIR CLEANING DEVICE

FIELD OF THE INVENTION

The invention relates to air cleaning systems, in particular to electric air cleaners, and it may be used for decontamination of air in different industries.

CONVENTIONAL ART

There are known tubular industrial electric air filters, where a coronizing electrode in form of a wire having diameter of 1.5 to 2.2 millimeters is located along axis of a collecting electrode provided in form of a tube (see pages 49-50 of [1]).

A limitation of this known solution is use of constant high voltage to generate a constant current corona discharge.

SUMMARY OF THE INVENTION

The invention is directed to attaining a technical effect of providing an air cleaning device, where air is cleaned owing to action of corona discharge streamers on air molecules and contamination particles.

The technical effect is attained by an air cleaning device that contains a high-voltage pulse generator, an outer electrode provided in form of a grounded metal tube, an inner electrode provided in form of a metal rod rigidly secured along the tube axis by a fastening member and configured so as pulsed corona discharge streamers are formed in between the inner and outer electrodes. The inner electrode is spaced by a gap from an output electrode of the high-voltage pulse generator, wherein size of the gap assures disruption of the gap with pulses formed by the high-voltage pulse generator.

Preferably, the output electrode of the high-voltage pulse generator is provided in form of a tip directed to the inner electrode.

Preferably, the inner electrode is provided with a tip directed to the output electrode of the high-voltage pulse generator.

Preferably, the inner electrode is provided in form of a metal rod having diameter of 2.5 to 5 millimeters.

Preferably, the length of the outer electrode tube is 1 to 1.5 meters and inner diameter thereof is 200 to 300 millimeters.

Preferably, the inner electrode is provided with ends thereof extending for 50 to 100 millimeters beyond the outer electrode tube.

Preferably, the fastening member of the inner electrode is provided in form of a one- or two- or three-thread screw electrically connected to the inner electrode and secured on a portion of the inner electrode inside the outer electrode tube, wherein the screw surface is formed by a metal strip with outer edge attached to the outer electrode via isolating members.

Preferably, the device is configured so as the size of the gap between ends of the inner electrode and the output electrode of the high-voltage pulse generator may be adjusted.

Preferably, the device may be connected to a gas removal system that provides passing a flow of air to be cleaned through the device from the high-voltage pulse generator side.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows a schematic diagram of an air cleaning device, where the following designators are used:
- 1—outer electrode in form of a metal tube;
- 2—inner electrode;
- 3—high-voltage pulse generator;
- 4—output electrode of high-voltage pulse generator;
- 5—gap between ends of electrodes 2 and 4;
- 6—fastening member of inner electrode in form of one-thread screw;
- 7—isolating members;
- 8—blade of one-way auger;
- 9—flow of contaminated air;
- 10—flow of decontaminated air.

DETAILED DESCRIPTION OF EMBODIMENTS OF THE INVENTION

Reference will now be made in detail to the preferred embodiments of the present invention, examples of which are illustrated in the accompanying drawings.

FIG. 1 shows a schematic diagram of an air cleaning device, where the following designators are used:
- 1—outer electrode in form of a metal tube;
- 2—inner electrode;
- 3—high-voltage pulse generator;
- 4—output electrode of high-voltage pulse generator;
- 5—gap between ends of electrodes 2 and 4;
- 6—fastening member of inner electrode in form of one-thread screw;
- 7—isolating members;
- 8—blade of one-way auger;
- 9—flow of contaminated air;
- 10—flow of decontaminated air.

The invention may be implemented as a device comprising a high-voltage pulse generator (3), an outer electrode (1) provided in form of a grounded metal tube and an inner electrode (2) installed along axis of the tube using a fastening member (6) and spaced by a gap (5) from an output electrode (4) of the high-voltage pulse generator. The fastening member (6) of the inner electrode (2) is provided in form of a one-way auger with a blade (8) attached to the outer electrode (1) via isolating members (7). The device is connected to a gas removal system (not shown in drawings) that provides motion of a flow of air to be cleaned through the device from side where the output electrode (4) of the high-voltage pulse generator (3) is located.

The device operates as follows. A contaminated air flow (9) is fed into the device. The high-voltage pulse generator (3) provides a high-voltage pulse to the output electrode (4). When voltage of the output electrode (4) exceeds a breakdown voltage of the gap (5), disruption of the gap (5) takes place and the high-voltage pulse reaches the inner electrode (2) with the blade (8). As known from [2], corona discharge streamers occur between the inner electrode (2) with the blade (8) and the outer electrode (1) at each pulse, which cause formation of plural charged particles in the area between the inner and outer electrodes and charging contamination particles in the air. The contamination particles are attracted to the outer electrode that has opposite electrical charge due to electrostatic induction, so the contamination particles are removed from the contaminated air flow (9). Simultaneously, plasma of corona discharge streamers affects water molecules contained in the air to be cleaned and causes formation of free radicals upon destruction of these molecules: $H_2O \rightarrow OH\cdot + H\cdot$. Moreover, other active substances like $O_3$, $O_2(a^1\Delta)$, $H_2O_2$, OH, $O(^3P)$, NO, $HNO_2$ and $HNO_3$ are formed due to action of corona discharge streamers on molecules of air. Streamer corona discharge also causes ultraviolet (UV) radiation. The above-mentioned active substances and UV radiation destroy any organic substances contained in the air to be cleaned, thus providing complete destruction thereof and formation of harmless gaseous products, namely, water and carbon dioxide. Oxidation process in water for organic substances is a chain reaction [3]. Non-organic substances deposited on the outer electrode (1) are destroyed by generated acids. A low rate chain reaction may be initiated by atmospheric oxygen and ozone. A high rate chain reaction is initiated by OH· radicals. In other words, plasma-chemical destruction of both organic and inorganic substances contained in the contaminated air flow (9) is provided in the device. A decontaminated air flow (10) leaves the device.

Thus, the technical effect is attained, which consists in providing an air cleaning device, where air cleaning is assured by action of pulsed corona discharge streamers on air molecules and contamination particles.

Having thus described a preferred embodiment, it should be apparent to those skilled in the art that certain advantages of the described method and apparatus have been achieved.

It should also be appreciated that various modifications, adaptations, and alternative embodiments thereof may be made within the scope and spirit of the present invention. The invention is further defined by the following claims.

LIST OF INFORMATION SOURCES

[1] Ecotechnics, *Equipment for cleaning processes for industrial gases and liquids: A study guide*/D. E. Smirnov (et al.); gen. ed. by L. V. Chekalov, A. V. Sugak.-Yaroslavl: YaGTU publ., 2013.-180 pages. ISBN 978-5-9914-0351-1.

[2] Aristova N. A., Piskarev I. M., Ivanovskiy A. V., Selemir V. D., Spirov G. M., Shlepkin S. I., *Initiation of chemical reactions by electrical discharge in dielectric-gas-liquid configuration*//Physical Chemistry Journal, 2004, Vol. 78, #7, pages 1326-1331.

Piskarev I. M., *Oxidation-reduction processes in water initiated by electrical discharge above water surface*//General Chemistry Journal, 2001, Vol. 71, Issue 10, page 1622.

What is claimed is:

1. An air cleaning device comprising:
a high-voltage pulse generator having an output electrode;
an outer electrode shaped as a metal tube; and
an inner electrode that is at least as long as the metal tube, wherein the inner electrode is spaced by a gap from the output electrode of the high-voltage pulse generator, wherein the gap is located outside the metal tube,
wherein the outer electrode is grounded,
wherein the inner electrode is shaped as a metal rod and is rigidly secured along an axis of the metal tube using an auger that is electrically connected to the inner electrode and secured on a portion of the inner electrode inside the outer electrode, wherein a surface of a blade of the auger is formed by a metal strip, and an outer edge of the metal strip is attached to the outer electrode and is electrically insulated from the outer electrode,
wherein the inner and outer electrodes are configured so that pulsed corona discharge streamers are formed in between the inner and outer electrodes, and
wherein a size of the gap assures breakdown of the gap with pulses formed by the high-voltage pulse generator.

2. The air cleaning device of claim 1, wherein the output electrode of the high-voltage pulse generator is shaped as a tip directed to the inner electrode.

3. The air cleaning device of claim 1, wherein the inner electrode includes a tip directed toward the output electrode of the high-voltage pulse generator.

4. The air cleaning device of claim 1, wherein the metal rod has a diameter of 2.5 to 5 millimeters.

5. The air cleaning device of claim 1, wherein a length of the outer electrode is 1 to 1.5 meters and an inner diameter of the outer electrode is 200 to 300 millimeters.

6. The air cleaning device of claim 1, wherein ends of the inner electrode extend for a distance of 50 to 100 millimeters beyond the outer electrode.

7. The air cleaning device of claim 1, wherein a size of the gap is adjustable.

8. The air cleaning device of claim 1, wherein a flow of air to be cleaned is from a side where the high-voltage pulse generator is located.

9. An air cleaning device comprising:
a high-voltage pulse generator having an output electrode;
an outer electrode shaped as a metal tube and grounded; and
an inner electrode extending an entire length of the metal tube, wherein the inner electrode is separated from the output electrode by a gap,
wherein the inner electrode is shaped as a metal rod and is rigidly secured along an axis of the metal tube using an auger that is electrically connected to the inner electrode and secured on a portion of the inner electrode inside the outer electrode, wherein a surface of a blade of the auger is conductive, and the auger is attached to the outer electrode and is electrically insulated from the outer electrode.

* * * * *